United States Patent
Hirose et al.

(10) Patent No.: US 9,410,906 B2
(45) Date of Patent: Aug. 9, 2016

(54) X-RAY FLUORESCENCE SPECTROMETER COMPRISING A TEMPERATURE SENSOR, TWO EXTERNAL-AIR FANS, AND A CIRCULATION FAN

(71) Applicant: Hitachi High-Tech Science Corporation, Minato-ku, Tokyo (JP)

(72) Inventors: Ryusuke Hirose, Tokyo (JP); Haruo Takahashi, Tokyo (JP); Yoshiki Matoba, Tokyo (JP); Koichi Tamura, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 202 days.

(21) Appl. No.: 14/221,535

(22) Filed: Mar. 21, 2014

(65) Prior Publication Data

US 2014/0294145 A1    Oct. 2, 2014

(30) Foreign Application Priority Data

Mar. 27, 2013  (JP) ................ 2013-065714

(51) Int. Cl.
*G01N 23/223*  (2006.01)
*H05G 1/02*  (2006.01)

(52) U.S. Cl.
CPC ............ *G01N 23/223* (2013.01); *H05G 1/025* (2013.01); *G01N 2223/076* (2013.01); *G01N 2223/31* (2013.01)

(58) Field of Classification Search
CPC . G01N 23/2076; G01N 23/22; G01N 23/223; G01N 2223/076; G01N 2223/31; G01N 2223/3103; G01N 2223/3106; H05G 1/025; H01J 35/105; H01J 35/106; H01J 35/12

USPC ............ 378/44–50, 130, 141, 199, 200
See application file for complete search history.

(56) References Cited

U.S. PATENT DOCUMENTS 5,740,223 A * 4/1998 Ozawa ............. G01N 23/223
378/161
5,937,026 A * 8/1999 Satoh ............. G01N 23/223
378/44

(Continued)

FOREIGN PATENT DOCUMENTS

| CN | 202710494 U | 1/2013 |
| JP | H10-234722 A | 9/1998 |
| JP | 2011-071120 A | 4/2011 |

OTHER PUBLICATIONS

Aug. 1, 2014—(EP) Extended Search Report—App 14161051.9.

(Continued)

*Primary Examiner* — Allen C. Ho
(74) *Attorney, Agent, or Firm* — Banner & Witcoff, Ltd.

(57) ABSTRACT

An X-ray fluorescence spectrometer includes: an X-ray source which irradiates a sample with primary X-rays; a light condensing device which condenses the primary X-rays to reduce an irradiation area on the sample; a detector which detects fluorescent X-rays produced from the sample irradiated with the primary X-rays; a housing which accommodates the X-ray source and the light condensing device; a temperature sensor which is disposed in at least one of the X-ray source and the periphery of the X-ray source; at least one external-air fan which is disposed on the housing, and which can exchange internal air with external air; and a control section which drives the external-air fan based on temperature information detected by the temperature sensor, to adjust the ambient temperature around the X-ray source to a constant temperature.

8 Claims, 1 Drawing Sheet

(56) References Cited

U.S. PATENT DOCUMENTS

| | | | | |
|---|---|---|---|---|
| 6,052,431 A * | 4/2000 | Onoguchi | G21K 1/06 | 378/145 |
| 6,108,398 A * | 8/2000 | Mazor | G01N 23/223 | 378/45 |
| 6,263,046 B1 * | 7/2001 | Rogers | F28D 15/02 | 378/140 |
| 6,345,086 B1 * | 2/2002 | Ferrandino | G01N 23/223 | 378/206 |
| 6,453,002 B1 * | 9/2002 | Mazor | G01N 23/223 | 378/49 |
| 6,519,317 B2 * | 2/2003 | Richardson | H01J 35/106 | 378/130 |
| 6,577,705 B1 * | 6/2003 | Chang | G01N 23/223 | 378/45 |
| 6,697,454 B1 * | 2/2004 | Nicolich | G21K 1/06 | 378/48 |
| 6,754,304 B1 * | 6/2004 | Kumakhov | G01N 23/223 | 378/45 |
| 6,934,359 B2 * | 8/2005 | Chen | B82Y 10/00 | 378/45 |
| 6,963,632 B2 * | 11/2005 | Kendall | H05G 1/025 | 378/141 |
| 6,965,663 B2 * | 11/2005 | Ohzawa | G01N 23/223 | 250/505.1 |
| 6,997,609 B2 * | 2/2006 | McCarthy, Jr. | A61B 6/035 | 378/141 |
| 7,023,954 B2 * | 4/2006 | Rafaeli | G01N 23/22 | 378/206 |
| 7,072,439 B2 * | 7/2006 | Radley | G01N 23/12 | 378/47 |
| 7,072,445 B2 * | 7/2006 | Kendall | A61B 6/035 | 378/141 |
| 7,209,545 B2 | 4/2007 | Radley et al. | | |
| 7,298,817 B2 * | 11/2007 | Chen | G01N 23/223 | 378/44 |
| 7,409,037 B2 * | 8/2008 | Puusaari | G01N 23/223 | 378/44 |
| 7,416,333 B2 * | 8/2008 | Zhang | F04D 29/541 | 378/199 |
| 7,443,959 B2 * | 10/2008 | Kantonen | G01N 23/223 | 378/147 |
| 7,508,906 B2 * | 3/2009 | Puusaari | G01N 23/223 | 378/157 |
| 7,508,907 B2 * | 3/2009 | Sasayama | G01N 23/223 | 378/149 |
| 7,543,987 B2 * | 6/2009 | Canfield | A61B 6/40 | 378/141 |
| 7,587,025 B2 * | 9/2009 | Fukai | G01N 23/223 | 378/149 |
| 7,796,726 B1 * | 9/2010 | Gendreau | G01N 23/20 | 378/44 |
| 7,970,101 B2 * | 6/2011 | Sakai | G01N 23/223 | 378/44 |
| 8,000,439 B2 * | 8/2011 | Matoba | G01N 23/223 | 378/44 |
| 8,355,126 B2 * | 1/2013 | Goulter | G01J 3/02 | 356/313 |
| 8,475,042 B1 * | 7/2013 | Reilly | G01N 23/223 | 378/142 |
| 2004/0057553 A1 | 3/2004 | Kendall et al. | | |
| 2005/0031073 A1 | 2/2005 | Radley et al. | | |
| 2005/0041773 A1 | 2/2005 | Gibson et al. | | |
| 2005/0053197 A1 | 3/2005 | Radley et al. | | |

OTHER PUBLICATIONS

R: "Practical tips from Rittal Enclosure climate control and machine cooling Contents", Oct. 30, 2007, XP055130257, D-35726 Herborn, Retrieved from the Internet: <URL:http://www.rittal.de/down]oads/TechInfo/en/8718_SK_Praxi stips_GB.pdf> [retrieved on Jul. 18, 2014] *p. 13*, 44 pages.

* cited by examiner

X-RAY FLUORESCENCE SPECTROMETER COMPRISING A TEMPERATURE SENSOR, TWO EXTERNAL-AIR FANS, AND A CIRCULATION FAN

This application claims priority from Japanese Patent Application No. 2013-065714 filed on Mar. 27, 2013, the entire subject-matter of which is incorporated herein by reference.

BACKGROUND

1. Technical Field

The present disclosure relates to an X-ray fluorescence spectrometer which can perform detection of a hazardous substance or the like, and which is used for, for example, screening products, or measuring the film thickness of plating or the like.

2. Description of the Related Art

In the X-ray fluorescence spectroscopy, a sample is irradiated with X-rays emitted from an X-ray source, and fluorescence X-rays which are characteristic X-rays released from the sample are detected by an X-ray detector. A spectrum is obtained from the energy of the detected X-rays, and the sample is qualitatively or quantitatively analyzed, or the film thickness is measured. In the X-ray fluorescence spectroscopy, a sample can be rapidly analyzed in a non-destructive manner. Therefore, the X-ray fluorescence spectroscopy is widely used in the process and quality management or the like. Recently, the accuracy and sensitivity of the X-ray fluorescence spectroscopy have been improved, so that micro measurement can be performed. The X-ray fluorescence spectroscopy is therefore expected to be in widespread use as an analysis technique for detecting a hazardous substance which may be contained in, particularly, a material, a composite electronic component, or the like.

Among X-ray fluorescence spectrometers, known is a spectrometer including a polycapillary optic which can condense X-rays emitted from an X-ray source to reduce the irradiation area on a sample. A polycapillary optic is an X-ray condensing device which is configured by a bundle of glass tubes (capillaries) each having a diameter of about 10 μm, and which has a lens function of causing incident X-rays to be totally internally reflected, and condensing and emitting the X-rays.

For example, JP-A-2011-71120 discloses an X-ray source assembly including an X-ray tube and a polycapillary optic which is an X-ray optical device for collecting X-rays emitted from the X-ray tube. The X-ray source assembly includes a temperature actuator which, in order to adjust the position, directly heats or cools the target of the X-ray tube.

SUMMARY

The above-described related art has some disadvantages.

In an apparatus in which a polycapillary optic is attached to a bulb of an X-ray source, the intensity of the output of the polycapillary optic depends on the attachment position thereof. Thus, there may be a problem in that, if a positional deviation occurs, the output intensity is reduced. Even when a polycapillary optic is relatively deviated in a horizontal direction only by 10 μm, for example, the output intensity is reduced by 5%. In order to perform a measurement at a stable output intensity, therefore, the polycapillary optic must be attached to a portion where the maximum output intensity is obtained, and it is indispensable that the polycapillary optic is prevented from deviating from the position to which it is once attached. Causes of deviation of the position of a polycapillary optic are a mechanical cause and a cause due to heat (temperature drift). Particularly, an electric power of 30 to 50 W is usually applied to a bulb of an X-ray source, and therefore its temperature is largely changed when the electric power is changed. Also the ambient temperature of the spectrometer is changed in a range of 10 to 30° C. unless the ambient temperature is specially controlled. Thermal expansion due to such temperature changes causes the polycapillary optic to be relatively positionally deviated, and hence there is a disadvantage that the output intensity is varied.

By contrast, in the technique disclosed in JP-A-2011-71120, in order to suppress the variation of the output intensity due to a temperature change, when the ambient temperature is changed, a positional correction due to a temperature change is performed by directly heating/cooling the target (anode) of the bulb by a temperature actuator to move the position. However, the disposition of the temperature actuator in the target of the bulb causes problems in that the structure is complicated, that the control is difficult, and that the production cost is increased.

Illustrative aspects of the invention provide an X-ray fluorescence spectrometer in which a variation of the output intensity can be suppressed by a configuration and control that are relatively simple.

According to a first illustrative aspect of the invention, there may be provided an X-ray fluorescence spectrometer comprising: an X-ray source configured to irradiate a sample with primary X-rays; a light condensing device configured to condense the primary X-rays emitted from the X-ray source to reduce an irradiation area on the sample; a detector configured to detect fluorescent X-rays produced from the sample irradiated with the primary X-rays; a housing which accommodates at least the X-ray source and the light condensing device; a temperature sensor which is disposed in at least one of the X-ray source and a periphery of the X-ray source; at least one external-air fan, which is disposed on the housing, and which is configured to exchange internal air with external air; and a control section configured to drive the external-air fan based on temperature information detected by the temperature sensor so as to adjust an ambient temperature around the X-ray source to a constant temperature.

In the X-ray fluorescence spectrometer, the control section drives the external-air fan based on the temperature information detected by the temperature sensor, to adjust the ambient temperature around the X-ray source to a constant temperature. Unlike the prior art, therefore, a part of the X-ray source is not temperature-controlled, but the whole ambience around the X-ray source is temperature-controlled so as to have a constant temperature, whereby a temperature variation can be eliminated as a whole, and a positional deviation can be suppressed. Consequently, it is not required to complicate the structure by directly incorporating a temperature control mechanism into the X-ray source, and the temperature variation between the X-ray source and the polycapillary optic can be suppressed by the configuration and control which are relatively simple, and which are configured by the X-ray source functioning as a heat source, and the external-air fan for exchanging the air. As a result, the variation of the output intensity due to a positional deviation can be suppressed.

According to a second illustrative aspect of the invention, the X-ray fluorescence spectrometer according to the first illustrative aspect may further comprise a circulation fan that is disposed in a periphery of the X-ray source, wherein the control section is configured to perform the adjustment of the ambient temperature by further driving the circulation fan.

In the X-ray fluorescence spectrometer, namely, the control section performs the adjustment by driving also the circulation fan. In the case where, for example, the cooling effect is not sufficiently obtained by driving only the external-air fan, therefore, the circulation fan is driven in addition to the external-air fan, whereby the ambient air around the X-ray source is circulated, and a temperature difference due to air stagnation can be prevented from occurring.

According to a third illustrative aspect of the invention, the X-ray fluorescence spectrometer according to the first or the second illustrative aspect may further comprise a heater that is disposed between the external-air fan for introducing the external air and the X-ray source, wherein the control section is configured to perform the adjustment by further driving the heater.

In the X-ray fluorescence spectrometer, namely, the control section performs the adjustment by driving also the heater. Even in the case where the temperature of the external air introduced by the external-air fan is excessively low, or where the ambient temperature is not sufficiently raised only by the heat of the X-ray source itself, therefore, the introduced external air is heated by the heater to produce warm air, whereby the ambient temperature can be easily raised, and a temperature control which is more flexible is enabled.

According to a fourth illustrative aspect of the invention, in the X-ray fluorescence spectrometer according to any one of the first to the third illustrative aspects, the light condensing device may be a polycapillary optic.

According to a fifth illustrative aspect of the invention, in the X-ray fluorescence spectrometer according to any one of the first to the fourth illustrative aspects, the external-air fan may comprise: an air intake fan configured to introduce the external air into the housing; and an exhaust fan configured to discharge the internal air to outside.

According to a sixth illustrative aspect of the invention, in the X-ray fluorescence spectrometer according to the fifth illustrative aspect, the air intake fan may be configured to introduce the external air toward the X-ray source, the X-ray fluorescence spectrometer may further comprise a circulation fan that is disposed in a periphery of the X-ray source and is configured to circulate the air around the X-ray source, and the control section may be configured to perform the adjustment of the ambient temperature by selectively driving the air intake fan, the exhaust fan and the circulation fan based on temperature information detected by the temperature sensor.

According to a seventh illustrative aspect of the invention, in the X-ray fluorescence spectrometer according to the sixth illustrative aspect, the temperature sensor may be attached to the X-ray source and be configured to detect temperature of the X-ray source.

According to an eighth illustrative aspect of the invention, the X-ray fluorescence spectrometer according to the fifth illustrative aspect may further comprise a heater that is disposed between the air intake fan and the X-ray source and is configured to heat the air introduced by the intake fan, wherein the temperature sensor comprises: a first temperature sensor that is attached to the X-ray source and is configured to detect temperature of the X-ray source; and a second temperature sensor that is disposed between the heater and the X-ray source and is configured to detect temperature of the heated air, and wherein the control section is configured to perform the adjustment of the ambient temperature by selectively driving the air intake fan, the exhaust fan and the heater based on temperature information detected by the first temperature sensor and the second temperature sensor.

According to the X-ray fluorescence spectrometer of the illustrative aspects of the invention, the control section drives the external-air fan based on temperature information detected by the temperature sensor, to adjust the ambient temperature around the X-ray source to the constant temperature. Therefore, the temperature variation between the X-ray source and the polycapillary optic can be suppressed at a low cost by the configuration and control that are relatively simple, and the variation of the output intensity due to a positional deviation can be suppressed. Even when the temperature of the X-ray source or the periphery of the spectrometer is changed, consequently, the ambient temperature of the interior of the spectrometer can be kept constant to suppress the variation of the output intensity, so that a stable measurement is enabled.

DETAILED DESCRIPTION

Hereinafter, a first illustrative embodiment of the X-ray fluorescence spectrometer of the invention will be described with reference to FIG. 1.

Figure 1:
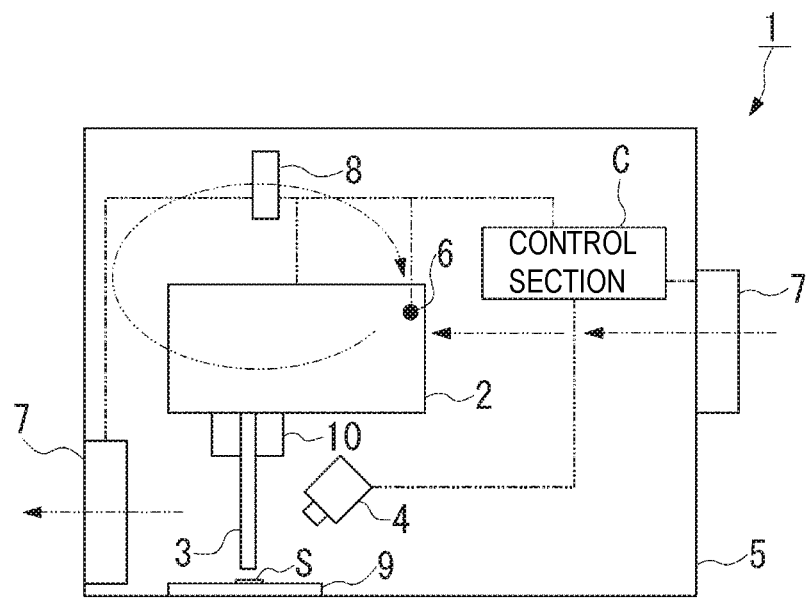
FIG. 1 is a whole configuration diagram showing a first illustrative embodiment of the X-ray fluorescence spectrometer of the invention.

As shown in FIG. 1, the X-ray fluorescence spectrometer 1 of the illustrative embodiment includes: an X-ray source 2 which irradiates a sample S with primary X-rays; a light condensing device 3 which condenses the primary X-rays emitted from the X-ray source 2 to reduce the irradiation area on the sample S; a detector 4 which detects fluorescent X-rays produced from the sample S irradiated with the primary X-rays; and a housing 5 which accommodates the X-ray source 2, the light condensing device 3, and the detector 4.

The X-ray fluorescence spectrometer 1 further includes: a temperature sensor 6 which is disposed in the X-ray source 2; two external-air fans 7 which are disposed on the housing 5, and which can exchange the internal air with the external air; a circulation fan 8 which is disposed in the periphery of the X-ray source 2; and a control section C which drives the two external-air fans 7 and the circulation fan 8 based on the temperature information detected by the temperature sensor 6, to adjust the ambient temperature around the X-ray source 2 to a constant temperature.

The X-ray source 2 is an X-ray bulb which can emit primary X-rays, and in which thermal electrons generated from the filament (cathode) in the bulb are accelerated by a voltage applied between the filament (cathode) and the target (anode), and collide against W (tungsten), Mo (molybdenum), Cr (chromium), or the like of the target to generate X-rays, and the X-rays are emitted as primary X-rays through a window configured by, for example, a beryllium foil.

The detector 4 includes a semiconductor detection device (for example, a Si (silicon) device that is a diode having the pin structure) (not shown) which is disposed in an X-ray entrance window. When one X-ray photon is incident on the detector 4, a current pulse corresponding to one X-ray photon is generated. The instantaneous current value of the current pulse is proportional to the energy of the incident X ray photon. Furthermore, the detector 4 is set so that the current pulse generated by the semiconductor detection device is converted to a voltage pulse, the voltage pulse being amplified, and the amplified voltage pulse being output as a signal.

The sample S is subjected to analysis while being placed on a sample stage 9 disposed in the housing 5.

The light condensing device 3 is a polycapillary optic which is attached to the X-ray source 2 through a position adjustment mechanism 10. In the light condensing device 3, the basal end is placed so that the primary X-rays emitted from the X-ray source 2 can be incident thereon, and the tip end from which the condensed primary X-rays are emitted is directed toward the sample stage 9. The position adjustment mechanism 10 is a known triaxial adjustment mechanism which holds the basal end of the light condensing device 3, and which adjusts the relative positions of the X-ray source 2 and the light condensing device 3 so that the maximum output intensity is obtained. As the light condensing device 3, a monocapillary optic, a collimator, or a polycapillary optic is preferably used. Alternatively, a focusing crystal or the like may be used.

As the temperature sensor 6, for example, a thermistor device or the like is employed. The sensor is disposed outside the X-ray source 2.

The two external-air fans 7 are disposed on opposing sidewalls of the housing 5, respectively. The two external-air fans 7 are driven such that one of the two external-air fans 7 (e.g., an air intake fan) is rotated in the direction in which the external air is sucked and introduced into the housing, and the other fan (e.g., an exhaust fan) is rotated in the direction in which the internal air is discharged to the outside.

The control section C is a computer which is connected also to the X-ray source 2, the detector 4, and the sample stage 9 to control them, and which is configured by a CPU and the like.

The X-ray fluorescence spectrometer 1 of the illustrative embodiment further includes an analyzer (not shown) which is connected to the detector 4, and which analyzes the signal output from the detector 4. The analyzer is a multi-channel pulse height analyzer which obtains the height of the voltage pulse from the signal to produce an energy spectrum.

Next, a method of controlling the temperature in the X-ray fluorescence spectrometer 1 of the illustrative embodiment will be described.

In the case where the temperature of the external air around the X-ray fluorescence spectrometer 1 is within the range of 10 to 30° C., for example, the control section C drives and controls the two external-air fans 7 and the circulation fan 8 so that the temperature of the X-ray source 2 detected by the temperature sensor 6 becomes 33° C. In this way, the temperature is controlled so that the temperature detected by the temperature sensor 6 is little higher than the upper limit of the external air temperature.

In the case where the temperature detected by the temperature sensor 6 is lower than 33° C., the control section C drives only the circulation fan 8. Usually, the bulb of the X-ray source 2 operates at about 50 W, and the bulb itself has heat energy. Therefore, the X-ray source 2 has an effect that the ambient temperature of the interior of the housing 5 is raised by using the bulb as a heat source. Consequently, the heat of the X-ray source 2 is controlled so that the ambient temperature of the interior of the housing 5 becomes 33° C. by causing the air in the housing 5 to flow, by the circulation fan 8.

In the case where the temperature detected by the temperature sensor 6 is higher than 33° C., the control section C drives both the two external-air fans 7 and the circulation fan 8. Therefore, the external air having a lower temperature is introduced by the two external-air fans 7, and the ambient air in the housing 5 is circulated by the circulation fan 8, so that the ambient temperature can be lowered to 33° C.

In the X-ray fluorescence spectrometer 1 of the illustrative embodiment, as described above, the control section C drives the two external-air fans 7 based on the temperature information detected by the temperature sensor 6, to adjust the ambient temperature around the X-ray source 2 to the constant temperature. Unlike the prior art, therefore, a part of the X-ray source 2 is not temperature-controlled, but the whole ambience around the X-ray source 2 is temperature-controlled so as to have the constant temperature, whereby a temperature variation can be eliminated as a whole, and a positional deviation can be suppressed.

Consequently, it is not required to complicate the structure by directly incorporating a temperature control mechanism into the X-ray source 2, and the temperature variation between the X-ray source 2 and the light condensing device 3 can be suppressed by the configuration and control which are relatively simple, and which are configured by the X-ray source 2 functioning a heat source, and the two external-air fans 7 for exchanging the air. As a result, the variation of the output intensity due to a positional deviation can be suppressed.

Moreover, the control section C adjusts the temperature by driving also the circulation fan 8. In the case where, for example, the cooling effect is not sufficiently obtained by driving only the two external-air fans 7, therefore, the circulation fan 8 is driven in addition to the two external-air fans 7, whereby the ambient air around the X-ray source 2 is circulated, and a temperature difference due to air stagnation can be prevented from occurring.

Figure 2:
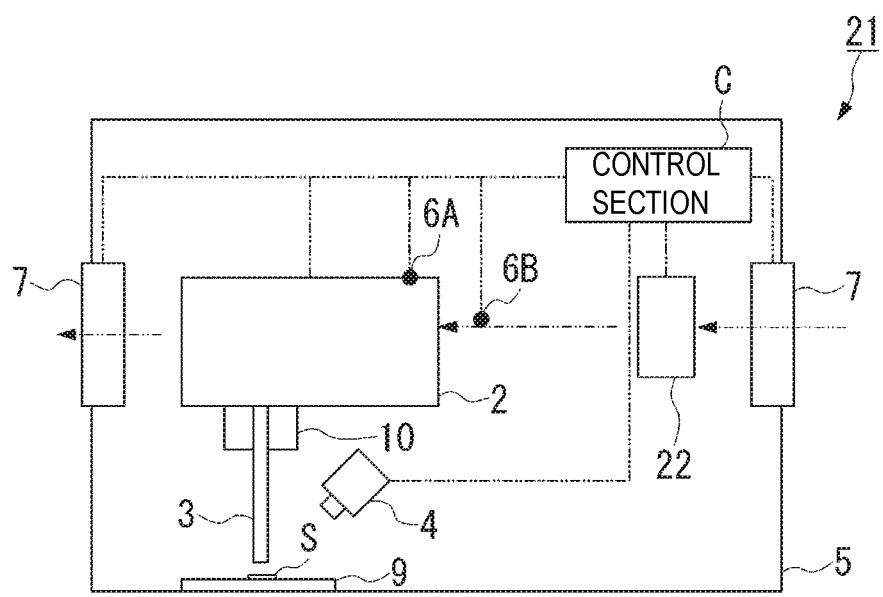
FIG. 2 is a whole configuration diagram showing a second illustrative embodiment of the X-ray fluorescence spectrometer of the invention.

Next, a second illustrative embodiment of the X-ray fluorescence spectrometer of the invention will be described with reference to FIG. 2. In the following description of the illustrative embodiment, the components which are identical with those in the above-described illustrative embodiment are denoted by the same reference numerals, and their description is omitted.

The second illustrative embodiment is different from the first illustrative embodiment in the following point. In the first illustrative embodiment, the temperature is adjusted by the fans such as the two external-air fans 7. By contrast, the X-ray fluorescence spectrometer 21 of the second illustrative embodiment includes a heater 22, which is disposed between the two external-air fans 7 for introducing the external air and the X-ray source 2 as shown in FIG. 2, and the control section C drives the heater 22 to adjust the temperature. In the second illustrative embodiment, the circulation fan 8 is not disposed.

The second illustrative embodiment is different from the first illustrative embodiment also in that two temperature sensors 6A, 6B are disposed. One of the temperature sensors or the temperature sensor 6A is attached to the X-ray source 2 in a similar manner as the first illustrative embodiment, and the other temperature sensor 6B is disposed in the periphery of the X-ray source 2 and between the heater 22 and the X-ray source 2. Therefore, the temperature sensor 6B can directly measure the temperature of the warm air which is supplied from the heater 22 toward the X-ray source 2.

In the X-ray fluorescence spectrometer 21 of the second illustrative embodiment, as described above, the control section C adjusts the temperature by driving also the heater 22. Even in the case where the temperature of the external air introduced by the two external-air fans 7 is excessively low, or where the ambient temperature is not sufficiently raised only by the heat of the X-ray source 2 itself, therefore, the introduced external air is heated by the heater 22 to produce warm air, whereby the ambient temperature can be easily raised, and a temperature control which is more flexible is enabled. In the second illustrative embodiment, particularly, the temperature of the warm air supplied to the X-ray source 2 is measured by the temperature sensor 6B, and the temperature adjustment is performed based on the two sets of information, i.e., the temperature information of the warm air, and that of the X-ray source 2 supplied from the temperature sensor 6A. Therefore, the ambient temperature of the whole housing 5 can be controlled more accurately.

The technical scope of the invention is not limited to the above-described illustrative embodiments, and various changes can be made without departing from the spirit of the invention.

For example, the invention may be configured such that the circulation fan 8 is provided to the above-described second exemplary embodiment. Further, the above-described illustrative embodiments are applied to an energy dispersive X-ray fluorescence spectrometer in which the energy and intensity of X-rays are measured by a pulse height analyzer, but alternatively, the invention may be applied also to a wavelength dispersive X-ray fluorescence spectrometer in which fluorescence X-rays are dispersed by an analyzing crystal, and the wavelength and intensity of the X-rays are measured.

What is claimed is:

1. An X-ray fluorescence spectrometer comprising:
   an X-ray source configured to irradiate a sample with primary X-rays;
   a light condensing device configured to condense the primary X-rays emitted from the X-ray source to reduce an irradiation area on the sample;
   a detector configured to detect fluorescent X-rays produced from the sample irradiated with the primary X-rays;
   a housing which accommodates at least the X-ray source and the light condensing device;
   a temperature sensor which is disposed in at least one of the X-ray source and a periphery of the X-ray source;
   at least one external-air fan, which is disposed on the housing, and which is configured to exchange internal air with external air; and
   a control section configured to drive the at least one external-air fan based on temperature information detected by the temperature sensor so as to adjust an ambient temperature around the X-ray source to a constant temperature.

2. The X-ray fluorescence spectrometer according to claim 1, further comprising:
   a circulation fan that is disposed in a periphery of the X-ray source,
   wherein the control section is configured to perform the adjustment of the ambient temperature by further driving the circulation fan.

3. The X-ray fluorescence spectrometer according to claim 1, further comprising:
   a heater that is disposed between the at least one external-air fan for introducing the external air and the X-ray source,
   wherein the control section is configured to perform the adjustment by further driving the heater.

4. The X-ray fluorescence spectrometer according to claim 1, wherein the light condensing device is a polycapillary optic.

5. The X-ray fluorescence spectrometer according to claim 1, wherein the at least one external-air fan comprises:
   an air intake fan configured to introduce the external air into the housing; and
   an exhaust fan configured to discharge the internal air to outside.

6. The X-ray fluorescence spectrometer according to claim 5,
   wherein the air intake fan is configured to introduce the external air toward the X-ray source,
   wherein the X-ray fluorescence spectrometer further comprises a circulation fan that is disposed in a periphery of the X-ray source and is configured to circulate the air around the X-ray source, and
   wherein the control section is configured to perform the adjustment of the ambient temperature by selectively driving the air intake fan, the exhaust fan and the circulation fan based on temperature information detected by the temperature sensor.

7. The X-ray fluorescence spectrometer according to claim 6, wherein the temperature sensor is attached to the X-ray source and is configured to detect temperature of the X-ray source.

8. The X-ray fluorescence spectrometer according to claim 5, further comprising:
   a heater that is disposed between the air intake fan and the X-ray source and is configured to heat the air introduced by the intake fan,
   wherein the temperature sensor comprises:
      a first temperature sensor that is attached to the X-ray source and is configured to detect temperature of the X-ray source; and
      a second temperature sensor that is disposed between the heater and the X-ray source and is configured to detect temperature of the heated air, and
   wherein the control section is configured to perform the adjustment of the ambient temperature by selectively driving the air intake fan, the exhaust fan and the heater based on the temperature detected by the first temperature sensor and the temperature detected by the second temperature sensor.

* * * * *